United States Patent [19]

Straussberger et al.

[11] 4,155,927

[45] May 22, 1979

[54] PROCESS FOR PREPARING TRIMETHYLCHLOROSILANE

[75] Inventors: Herbert Straussberger; Willi Streckel, both of Burghausen, Fed. Rep. of Germany

[73] Assignee: Wacker-Chemie GmbH, Munich, Fed. Rep. of Germany

[21] Appl. No.: 926,986

[22] Filed: Jul. 21, 1978

[30] Foreign Application Priority Data

Oct. 3, 1977 [DE] Fed. Rep. of Germany ....... 2744461

[51] Int. Cl.$^2$ .............................................. C07F 7/12
[52] U.S. Cl. ........................................... 260/448.2 E
[58] Field of Search ................................. 260/448.2 E

[56] References Cited

U.S. PATENT DOCUMENTS

| | | | |
|---|---|---|---|
| 2,403,370 | 7/1946 | Hurd | 260/448.2 E |
| 2,469,355 | 5/1949 | DePree et al. | 260/448.2 E |
| 2,598,436 | 5/1952 | Mohler et al. | 260/448.2 E |
| 2,626,269 | 1/1953 | Barry | 260/448.2 E |
| 4,053,495 | 10/1977 | Deinhammer et al. | 260/448.2 E |

*Primary Examiner*—Paul F. Shaver

[57] ABSTRACT

A process for preparing trimethylchlorosilane which comprises reacting methyldichlorosilane with methyl chloride and metallic aluminum.

2 Claims, No Drawings

PROCESS FOR PREPARING TRIMETHYLCHLOROSILANE

This invention relates to a process for preparing a chlorosilane and more particularly to a process for preparing trimethylchlorosilane from methyldichlorosilane.

BACKGROUND OF INVENTION

When silicon is reacted with methyl chloride, one of the products obtained as a result of the reaction and cleavage of the products having a boiling point about 75° C. at 760 mm Hg (abs) is methyldichlorosilane. Although methyldichlorosilane is very much in demand for preparing methylhydrogensiloxanes, trimethylchlorosilane and its derivatives are also very much in demand especially in the treatment of inorganic substances to impart hydrophobic properties thereto and to introduce end-blocking units in organopolysiloxane polymers. Moreover, trimethylchlorosilane is oftentimes in greater demand than methylhydrogensilane.

Therefore, it is an object of this invention to provide a process for preparing trimethylchlorosilane. A further object of this invention is to provide a process for preparing trimethylchlorosilane from methyldichlorosilane. The foregoing objects and others will become apparent from the following description.

SUMMARY OF INVENTION

The invention relates to a process for preparing trimethylchlorosilane which comprises reacting methyldichlorosilane with methyl chloride and metallic aluminum.

DETAILED DESCRIPTION OF INVENTION

In the process of this invention methyl chloride, which may also be referred to as monochloromethane, is preferably employed in amounts of from 0.5 to 4 mols per mol of methyldichlorosilane.

As used herein, the term "metallic aluminum" is intended to include aluminum metal as well as aluminum alloys containing at least 85 percent by weight of aluminum. An example of such an aluminum alloy is the one which is generally referred to as AlMgSi, having 0.6 to 1.4 percent by weight of Mg, 0.6 to 1.6 percent by weight Si, 0.6 to 1.0 percent by weight Mn, 0.0 to 0.3 percent by weight Cr with the remainder being Al. Other examples of aluminum alloys containing at least 85 percent by weight of aluminum are those which are briefly referred to as AlCuMg, AlCuMgPb, AlMg, AlMn, AlCuNi, AlSiCuNi and AlZnMg, as well as the various aluminum casting alloys. Additional details relating to these alloys are described in "Ullmanns Enchklopadie der technischen Chemie", vol. 3, Munich-Berlin 1953, pages 411 through 418.

It is preferred that the metallic aluminum be used in the form of powders, granules or agglomerations of granules.

Preferably, the metallic aluminum is employed in amounts of from 10 to 50 percent by weight, based on the weight of the methyldichlorosilane used.

The aluminum can be present as a stationary or fluidized bed.

In addition to methyldichlorosilane, methyl chloride and metallic aluminum, the reaction vessel may also contain powdered solid substances which under the reaction condtitions are relatively inert to the reactants and reaction products. Examples of such inert substances are silica gels, diatomite, silicates and aluminum oxide.

The process of this invention is preferably carried out at temperatures of from 180° to 450° C. and more preferably at temperatures of from 250° to 350° C.

It is preferred that the process be conducted at atmospheric pressure, i.e. at 1 bar or at approximately 1 bar to 35 bar.

The contact time of the aluminum and the reactants and the gaseous reaction products is preferably from 5 to 10 seconds and more preferably from 5 to 7 seconds.

In the following examples, all percentages are by weight unless otherwise specified.

EXAMPLE 1

A mixture consisting of 55 grams of methyldichlorosilane and 50 grams of methyl chloride is passed within one hour through a vertical glass tube containing a mixture consisting of 15 grams of aluminum powder ("Ecka AS 91"—available from the Eckardt Company, Furth, German Federal Republic) and 15 grams of diatomite which is agitated by means of a stirrer and heated to approximately 300° C. The mixture exiting from the glass tube is condensed and analyzed by gas chromatography. About 60 percent of the methyldichlorosilane is reacted and the following reaction products are obtained:

7.7 percent dimethyldichlorosilane
3.1 percent methyltrichlorosilane
76.8 percent trimethylchlorosilane
4.9 percent dimethylchlorosilane and 2-methylbutane
7.5 percent tetramethylsilane The above figures are average values obtained from the analysis of the reaction products after three runs.

EXAMPLE 2

A mixture containing 55 grams of methyldichlorosilane and 50 grams of methyl chloride is passed per hour through a vertical glass tube containing 15 grams of aluminum powder ("Ecka AS 91") and 15 grams of diatomite which is agitated by means of a stirrer while being heated to approximately 300° C. An additional 4 grams of aluminum powder is added to the glass tube every 15 minutes over a period of 2 hours. The mixture exiting from the glass tube is condensed and analyzed by gas chromatography. About 90 percent of the methyldichlorosilane is reacted and the following reaction products are obtained.

9.0 percent dimethyldichlorosilane
2.5 percent methyltrichlorosilane
81.7 percent trimethylchlorosilane
3.4 percent dimethylchlorosilane
3.4 percent tetramethylsilane The above figures represent average values obtained from the analysis of the reaction products obtained after three runs.

What is claimed is:

1. A process for preparing trimethylchlorosilane which comprises reacting methyldichlorosilane with methyl chloride and metallic aluminum.

2. The process of claim 1, wherein the reaction is conducted at a temperature of from 180° to 450° C.

UNITED STATES PATENT AND TRADEMARK OFFICE
CERTIFICATE OF CORRECTION

PATENT NO. : 4,155,927
DATED : May 22, 1979
INVENTOR(S) : Herbert Straussberger, Willi Streckel and
Dr. Rudolf Riedle It is certified that error appears in the above-identified patent and that said Letters Patent are hereby corrected as shown below:

Page 1, column 1, under "Inventors", after "Willi Streckel", delete "both" and insert ---Rudolf Riedle, all---

Signed and Sealed this

Fourth Day of December 1979

[SEAL]

Attest:

SIDNEY A. DIAMOND

Attesting Officer

Commissioner of Patents and Trademarks